United States Patent
Deo et al.

(10) Patent No.: US 12,048,419 B2
(45) Date of Patent: Jul. 30, 2024

(54) PEROXIDE-RESISTANT FLEXIBLE ENDOSCOPE, AND METHODS OF REPROCESSING OR STERILIZING SUCH ENDOSCOPE

(71) Applicant: HOYA CORPORATION, Tokyo (JP)

(72) Inventors: Hrishikesh Deo, Brooklyn, NY (US); Yusuke Iimori, Saitama (JP); Yasuhiro Sakai, Saitama (JP); Norimasa Okada, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 36 days.

(21) Appl. No.: 17/811,161

(22) Filed: Jul. 7, 2022

(65) Prior Publication Data
US 2024/0008722 A1   Jan. 11, 2024

(51) Int. Cl.
  *A61B 1/00*   (2006.01)
  *A61B 1/005*  (2006.01)

(52) U.S. Cl.
  CPC .......... *A61B 1/0057* (2013.01); *A61B 1/0008* (2013.01); *A61B 1/0011* (2013.01)

(58) Field of Classification Search
  CPC ... A61B 1/0057; A61B 1/0008; A61B 1/0011; A61B 1/0676; A61B 1/07; A61B 1/0052;
  (Continued)

(56) References Cited

U.S. PATENT DOCUMENTS

| 3,607,747 A | 9/1971 | Ishikawa et al. |
| 4,943,414 A | 7/1990 | Jacobs et al. |

(Continued)

FOREIGN PATENT DOCUMENTS

| JP | H1128184 A | 2/1999 |
| JP | 2004141272 A | 5/2004 |

(Continued)

OTHER PUBLICATIONS

"Cemedine Super A(Base resin)—Safety Data Sheet", Cemedine Co., Ltd., Jul. 27, 2012, 4 pages.
(Continued)

*Primary Examiner* — Timothy J Neal
*Assistant Examiner* — James Edward Boice
(74) *Attorney, Agent, or Firm* — Kilpatrick Townsend & Stockton LLP

(57) ABSTRACT

A peroxide-resistant endoscope comprises an interface portion; a control portion coupled to the interface portion; and an insertion portion coupled to the control portion. The insertion portion comprises a bending portion; an insertion tube extending from a distal end of the control portion to a proximal end of the bending portion; a bending portion coupled to a distal end of the insertion tube; and a distal tip at a distal end of the bending portion. The peroxide-resistant endoscope also comprises a light carrying bundle (LCB) that extends from the interface portion to the distal tip. An outer casing of the bending portion consists essentially of fluorocarbon rubber, the LCB is lubricated by a first lubricant that comprises at least one solid lubricant and does not contain more than ten percent by weight of molybdenum disulfide, and an outer casing of the insertion tube is bonded to the outer casing of the bending portion by an epoxy adhesive.

20 Claims, 5 Drawing Sheets

(58) Field of Classification Search
CPC .... A61B 1/005; A61B 1/00071; A61B 1/0055
USPC ........................................................ 600/139
See application file for complete search history.

(56) References Cited

U.S. PATENT DOCUMENTS

| | | |
|---|---|---|
| 5,026,607 A | 6/1991 | Kiezulas |
| 5,073,048 A | 12/1991 | Adachi et al. |
| 5,667,753 A | 9/1997 | Jacobs et al. |
| 5,674,450 A | 10/1997 | Lin et al. |
| 5,716,322 A | 2/1998 | Hui et al. |
| 5,785,934 A | 7/1998 | Jacobs et al. |
| 7,833,154 B2 | 11/2010 | Aono et al. |
| 10,973,392 B2 | 4/2021 | Furukawa et al. |
| 2002/0165431 A1 | 11/2002 | Muir et al. |
| 2003/0023143 A1 | 1/2003 | Abe et al. |
| 2006/0058583 A1 | 3/2006 | Matsumoto et al. |
| 2006/0173242 A1 | 8/2006 | Navok et al. |
| 2007/0282305 A1* | 12/2007 | Goldfarb ............... A61B 1/07 604/528 |
| 2009/0030280 A1 | 1/2009 | Matsumoto et al. |
| 2011/0245612 A1 | 10/2011 | Nakamura |
| 2013/0023920 A1 | 1/2013 | Terliuc et al. |
| 2013/0137928 A1 | 5/2013 | Karasawa et al. |
| 2016/0257906 A1* | 9/2016 | Kolekar ............... C10M 125/02 |
| 2016/0302645 A1 | 10/2016 | Miyagi et al. |
| 2016/0324576 A1* | 11/2016 | Ebbutt ............... A61B 18/1815 |
| 2019/0082937 A1* | 3/2019 | Hayashi ............... A61B 1/005 |
| 2019/0104924 A1* | 4/2019 | Okamoto ........... A61B 1/00071 |
| 2020/0100652 A1* | 4/2020 | Yoshitani ............ C08K 5/5415 |
| 2020/0187754 A1 | 6/2020 | Furukawa et al. |
| 2020/0187755 A1 | 6/2020 | Furukawa et al. |
| 2020/0246497 A1 | 8/2020 | Hara et al. |
| 2020/0246510 A1 | 8/2020 | Kobayashi et al. |
| 2021/0007579 A1 | 1/2021 | Furukawa et al. |
| 2021/0106210 A1 | 4/2021 | Nakai et al. |
| 2021/0179963 A1 | 6/2021 | Hara |
| 2021/0189203 A1 | 6/2021 | Furukawa et al. |
| 2021/0371714 A1 | 12/2021 | Furukawa et al. |
| 2021/0371715 A1 | 12/2021 | Furukawa et al. |
| 2021/0380834 A1 | 12/2021 | Nakai et al. |
| 2021/0380853 A1 | 12/2021 | Nakai et al. |
| 2022/0000346 A1 | 1/2022 | Switzer |
| 2022/0110506 A1 | 4/2022 | Morishima et al. |

FOREIGN PATENT DOCUMENTS

| | | |
|---|---|---|
| JP | 2004208962 A | 7/2004 |
| JP | 2006081749 A | 3/2006 |
| JP | 4130947 B2 | 6/2008 |
| JP | 2014033933 A | 2/2014 |
| WO | 2022070809 A1 | 4/2022 |

OTHER PUBLICATIONS

"Cemedine Super B(Hardener)—Safety Data Sheet", Cemedine Co., Ltd., Jul. 12, 2012, 3 pages.

"Vaprox HC Sterilant (59% Hydrogen Peroxide)—Safety Data Sheet", Steris, Jul. 25, 2014, 2 pages.

Fusaro et al., "Graphite fluoride as a solid lubricant in a polyimide binder", NASA Technical Note, NASA TN D-6714, Mar. 1972, 20 pages.

Lambert, "What is happening inside that magic box? Fundamentals of vaporized hydrogen peroxide sterilization in health care facilities", APIC, New York, New York, Sep. 20, 2021.

McDonnell, "Chemical disinfection and sterilization", Healthcare Purchasing News, Mar. 2014, 50-53.

Natoli, "Endoscopes and biocides", Microbiology Australia, Nov. 2010, 174-177.

Omidbakhsh et al., "Flexible gastrointestinal endoscope processing challenges, current issues and future perspectives", Journal of Hospital Infection 110, 2021, 133-138.

Robinson et al., "Using HPG sterilization for heat-sensitive devices", Healthcare Purchasing News, Jan. 2015, 30-33.

Talapa et al., "Vaporized Hydrogen Peroxide Sterilization", CRCST Self-Study Lesson Plan, Lesson No. CRCST 164 (Technical Continuing Education —TCE), 8 pages.

Yohanes et al., "The effect of epoxy/hardener composition ratio on the young's modulus of bulk adhesive at high strain rate", IOP Conference Series: Materials Science and Engineering 1034, 2021, 1-7.

PCT/US2023/027019, "International Search Report and the Written Opinion", Oct. 12, 2023, 8 pages.

* cited by examiner

PEROXIDE-RESISTANT FLEXIBLE ENDOSCOPE, AND METHODS OF REPROCESSING OR STERILIZING SUCH ENDOSCOPE

BACKGROUND

Field

The present disclosure generally relates to surgical devices, methods of fabrication of surgical devices, and methods of use of surgical devices. More particularly, and without limitation, the disclosed embodiments relate to peroxide-resistant flexible endoscopes, and methods for manufacture, assembly, or use of such devices.

Background

An endoscope is a surgical instrument that may be used to access (e.g., view or remove) or treat tissue within the body of a patient by inserting one or more medical tools into the body through an incision in the body or an orifice of the body.

SUMMARY

A peroxide-resistant flexible endoscope according to a general configuration comprises an interface portion; a control portion coupled to the interface portion; and an insertion portion coupled to the control portion. The insertion portion comprises a bending portion; an insertion tube extending from a distal end of the control portion to a proximal end of the bending portion; and a distal tip at a distal end of the bending portion. The peroxide-resistant flexible endoscope also comprises a light carrying bundle (LCB) that extends from the interface portion to the distal tip. An outer casing of the bending portion consists essentially of fluorocarbon rubber, the LCB is lubricated by a first lubricant that comprises at least one solid lubricant and does not contain more than ten percent by weight of molybdenum disulfide, and an outer casing of the insertion tube is bonded to the outer casing of the bending portion by an epoxy adhesive. Methods of reprocessing (e.g., cleaning, cleaning and disinfecting, cleaning and sterilizing, etc.) or sterilizing such endoscopes are also disclosed.

DETAILED DESCRIPTION

The disclosed embodiments include peroxide-resistant flexible endoscopes, and methods for reprocessing or sterilizing such endoscopes. Advantageously, embodiments of the present disclosure allow for endoscopes that may undergo many cycles of sterilization in an atmosphere of vaporized hydrogen peroxide without noticeable degradation.

As described herein, an endoscope typically includes a control portion (e.g., a handle) at a proximal end, a distal (or "sensing") end, an insertion tube that extends between the control portion and the distal end, and an interface portion that is coupled to the control portion by an umbilical cord. The term "proximal" (e.g., "a proximal end") refers to a point or a location along the length of the endoscope that is to be closer to a physician or other medical practitioner during use of the endoscope, and the term "distal" (e.g., "a distal end") refers to a point or location along the length of the endoscope that is to be closer to a location of tissue being viewed or treated within the body of a patient during use of the endoscope. Types of endoscope include, for example and without limitation, bronchoscopes, sinuscopes, nasopharyngoscopes, laryngoscopes, laparoscopes, gastroscopes, duodenoscopes, colonoscopes, echoendoscopes, hysteroscopes, cystoscopes, uroscopes, urethroscopes, cardioscopes, and arthroscopes.

Figure 1:
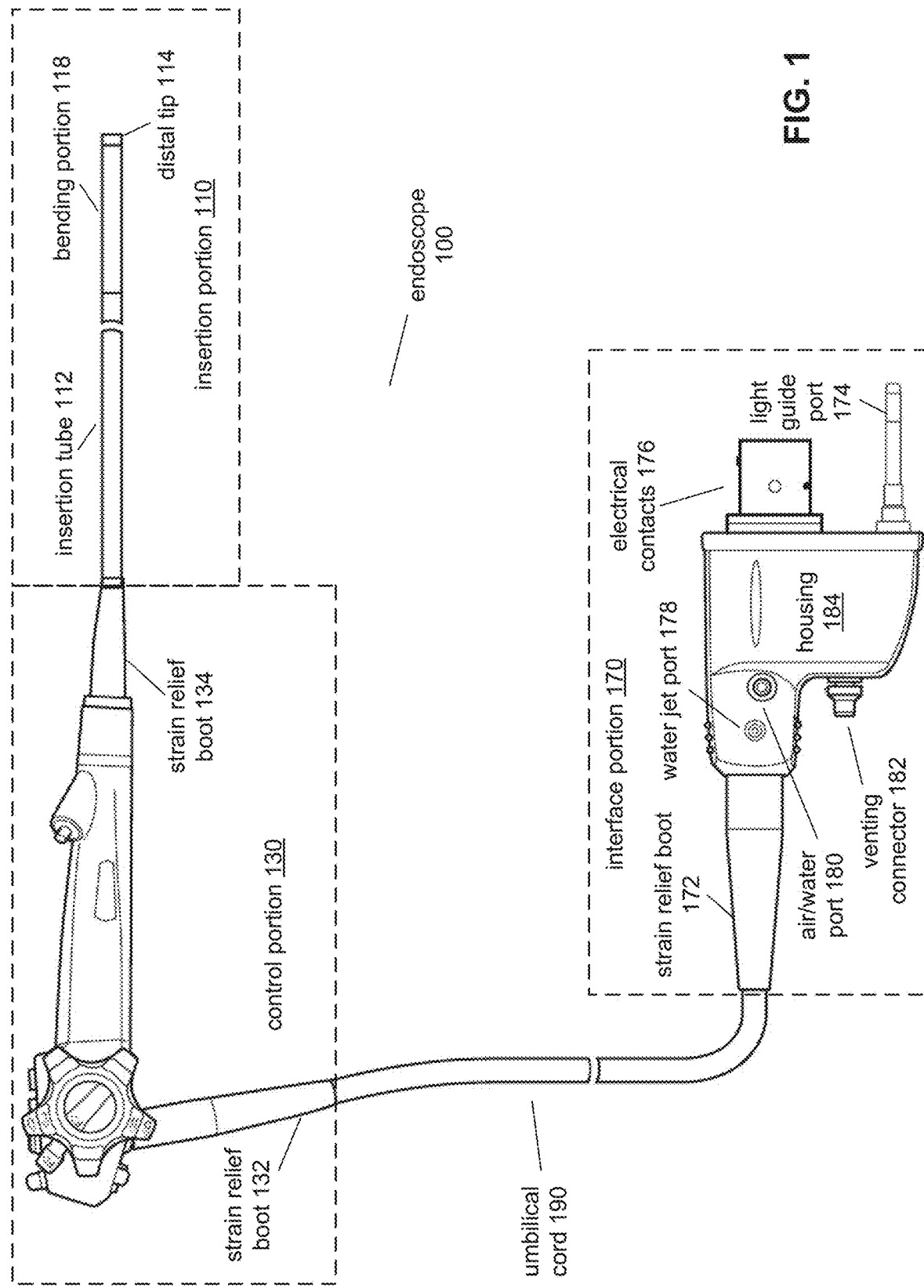
FIG. 1 is a diagram of a flexible endoscope in accordance with some embodiments.

FIG. 1 is a diagram of an endoscope 100 that may be implemented to be peroxide-resistant. As used herein, the term "peroxide-resistant" means that the endoscope may undergo many cycles of sterilization (e.g., fifty, one hundred, two hundred) in an atmosphere of vaporized hydrogen peroxide without developing at least some of the following defects, in some examples without developing any of the following defects: peeling, cracking, deformation, discoloration (e.g., bleaching), or failure of watertightness.

Endoscope 100 includes an insertion portion 110, a control portion 130, and an interface portion 170. Endoscope 100 is a flexible endoscope, which means that at least a portion of the insertion portion 110 (e.g., bending portion 118) is bendable with respect to a longitudinal axis of the insertion portion 110. The insertion portion 110 includes an insertion tube 112 that is coupled to the control portion 130 (e.g., to a strain relief boot 134), a distal tip 114, and a bending portion 118 that extends between the insertion tube 112 and the distal tip 114. The control portion 130 is connected to the interface portion 170 via an umbilical cord 190. In this example, the interface portion 170 includes a strain relief boot 172 that is bonded to the umbilical cord 190; a light guide plug or port 174; one or more electrical contacts 176, a water jet port 178, an air/water port 180, a venting connector 182, and a housing 184. In FIG. 1, the insertion portion 110 and the umbilical cord 190 are depicted with break lines to indicate that the lengths of these components have been shortened for illustration. In an endoscope for gastroenterological use (e.g., a gastroscope, a duodenoscope, a colonoscope), each of the insertion portion 110 and the umbilical cord 190 may have a length of up to approximately one or one-and-a-half meters.

Figure 2:
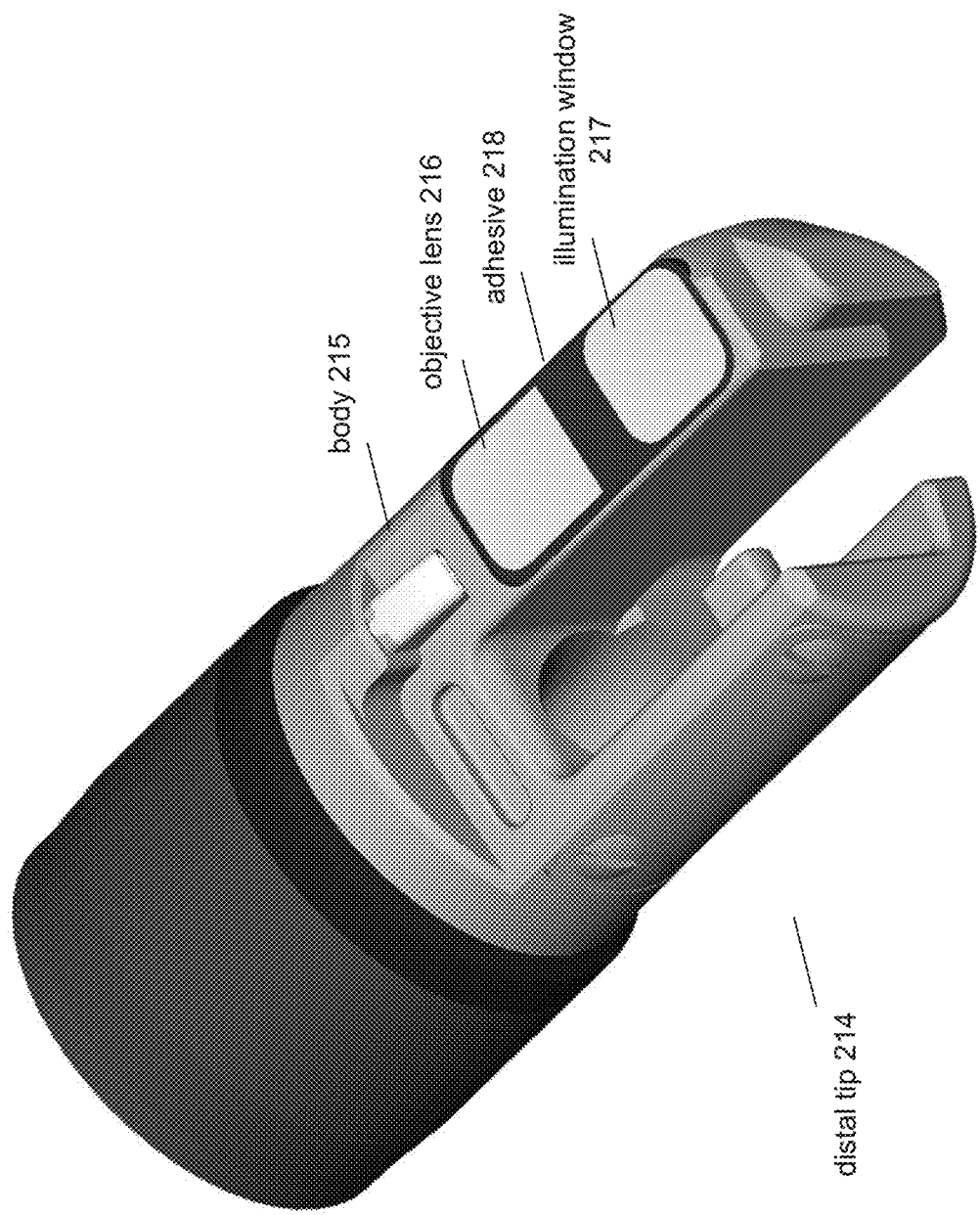
FIG. 2 is a diagram of an example of a distal tip of a flexible endoscope in accordance with some embodiments.

An endoscope includes a light carrying bundle or LCB, for example an optical waveguide bundle, in particular a light guide fiber bundle that comprises a large number of optical fibers and is encased within an elastomeric casing. In the following, reference is made to a light guide fiber bundle as an example of a light carrying bundle. In other examples, other types of waveguides may be used either instead of or in addition to optical fibers. The number of individual fibers (or waveguides) in the LCB may be in the range of from several hundred to more than one thousand, and each fiber in the LCB may have a diameter in the range of, for example, from about 0.01 to 0.03 mm. In the endoscope 100, the LCB extends from the interface portion of the endoscope (e.g., from light guide plug 174); through the umbilical cord 190, the control portion 130, and the insertion portion 110; to the distal tip 114, where it provides illumination to the working area within the patient's body via an optical glass window (also called an "illumination window") of the distal tip 114. FIG. 2 shows a diagram of an example 214 of distal tip 114 that includes an objective lens 216 and an illumination window 217 that are attached to a body 215 of the distal tip 214 by an adhesive 218.

The LCB may be flexible, and it may bend with the tubes (e.g., the umbilical cord 190, the insertion portion 110) through which it extends. Such bending of the LCB may cause the fibers within it to slide against each other, and friction generated by such movement may cause breakage of the fibers. The risk of fiber breakage due to bending may be especially high in the bending portion 118, as it may be desired to configure the bending portion 118 to bend to a small radius of curvature, e.g. less than 10 cm, in some examples less than 5 cm, in one examples less than 2 cm. To avoid fiber breakage by reducing friction against the fibers, the LCB is typically lubricated. For example, the fibers of the LCB may be coated with a lubricant to reduce friction between them. The lubricant may also be provided to reduce friction between the fibers and the inner surface of the casing of the LCB, and the outer surface of the casing of the LCB may be further lubricated to reduce friction between the LCB and other interior components of the endoscope (e.g., other tubes within the umbilical cord 190 and/or the insertion portion 110, such as a working channel, an air and/or water channel, etc.). In addition to protecting the fibers from breakage, such lubrication may also reduce the force required to bend a tube through which the LCB extends.

Figure 3:
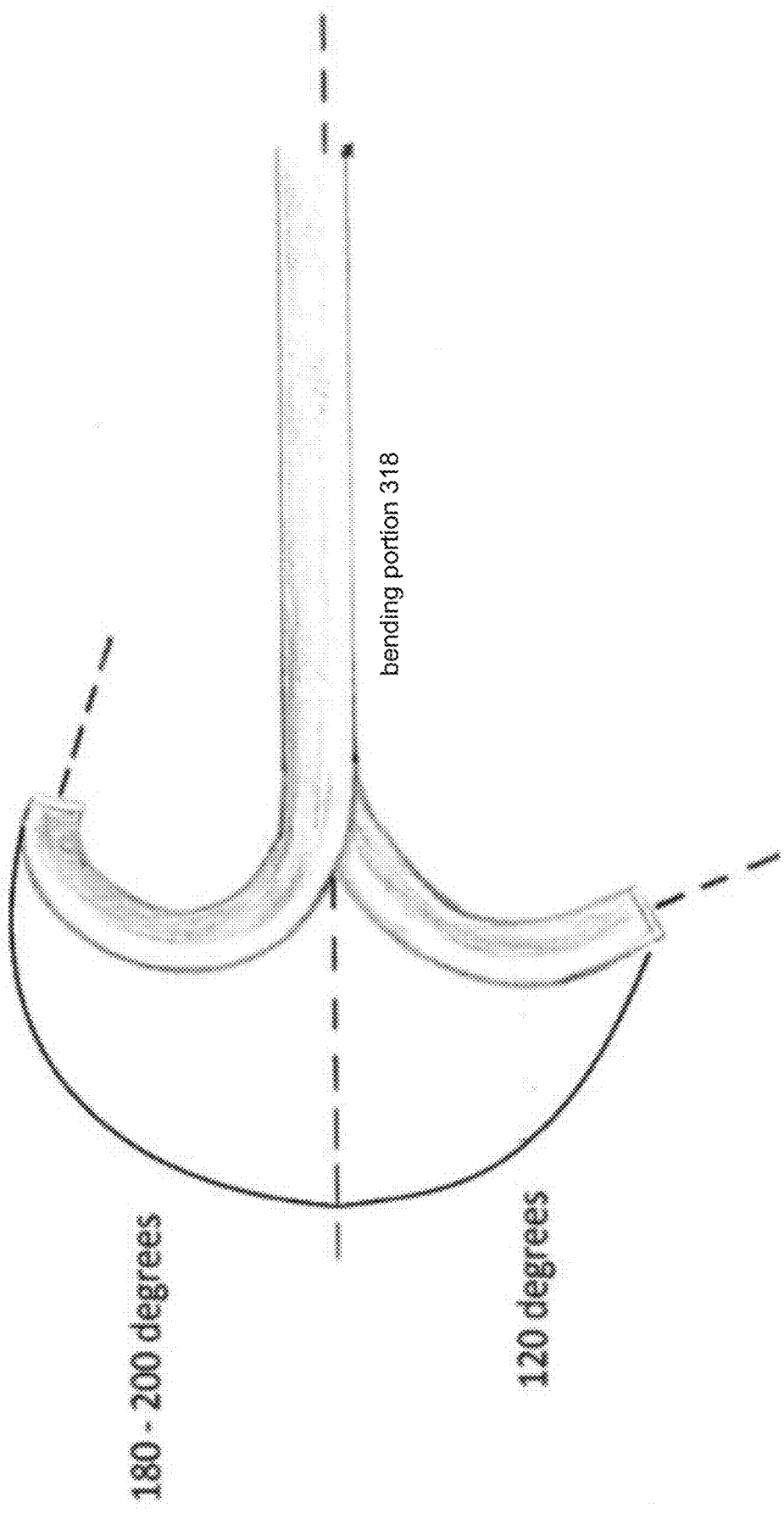
FIG. 3 is a diagram that shows an example of articulation of a bending portion of a flexible endoscope in accordance with some embodiments.

The bending portion 118 is configured to allow the distal tip 114 to move at least laterally (e.g., from side to side) relative to the insertion tube 112. For example, the bending portion 118 may have an inner skeleton comprising an elongated cylinder that is bendable in at least one direction and in at least one plane. Such an elongated cylinder may be formed by a series of substantially cylindrical tubular members (e.g., rings) that are pivotally connected along a central axis, or by some other articulable structure. In some implementations, the bending portion 118 is bendable in two directions in a plane (e.g., up and down). FIG. 3 shows a diagram of such an implementation 318 of the bending portion 118. In other implementations, the bending portion 118 is also bendable in a second plane that is perpendicular (or substantially perpendicular) to the first plane. In such case, for example, the bending portion 118 may be bendable in any of up, down, left, and right directions.

Such movement of the bending portion 118 may be controlled by an operator of the endoscope 100 by manipulating one or more actuators, e.g. control knobs, of the control portion 130. The force applied at the control portion 130 may e.g. be provided to the bending portion 118 by one or more angulation wires (also called "control wires"). The angulation wire(s) extend from the control portion 130 (e.g., from one or more actuators, which may be knobs or levers), through the insertion portion 110, to the distal end of the bending portion 118.

Figure 4:
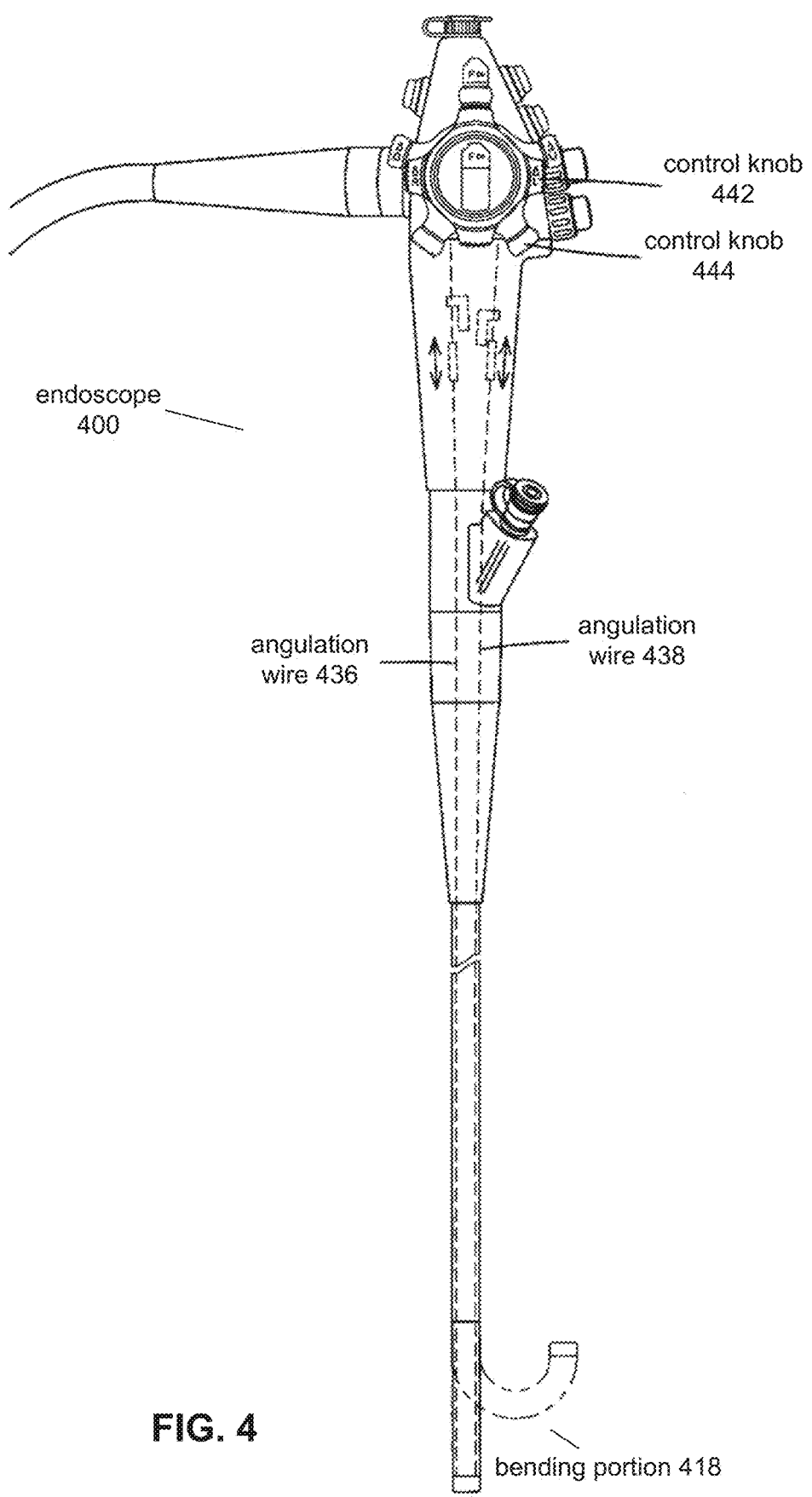
FIG. 4 is a diagram that shows angulation wires of a flexible endoscope in accordance with some embodiments.

FIG. 4 shows an example 400 of the endoscope 100 that includes angulation wires 436 and 438. In this example, the angulation wires 436 and 438 cause the bending portion 418 to bend in response to force applied (e.g., by an operator of the endoscope) by rotating one or both of control knobs 442 and 444. In order to reduce the amount of force that must be applied at the control portion 130 to achieve a desired movement of the bending portion 118, the surfaces of the angulation wires may be coated with lubricant.

Because an endoscope is used within the body, it is expected that it will become contaminated by such use and must undergo reprocessing (e.g., cleaning, disinfection, and/or sterilization) before the next use. Cleaning of the endoscope may include soaking the endoscope in a cleaning solution (e.g., a solution containing at least one detergent and/or enzymatic cleaning agent) and may also include mechanical cleaning such as brushing of one or more interior channels of the endoscope and/or wiping of the exterior of the endoscope (e.g., with gauze and/or with a sponge).

Additionally or in the alternative, cleaning of an endoscope may include injecting, into the interior lumen of a channel of the endoscope, a flow of a dispersion (e.g., a suspension), in a gas, of fine droplets of a liquid. The gas may comprise or consist essentially of, for example, one or more of air, dinitrogen, or carbon dioxide. The liquid may comprise or consist essentially of, for example, one or more of osmosed water, distilled water, deionized water, or purified water (e.g., type II laboratory grade purified water). In one example, a concentration of surfactants in the liquid does not exceed 2 mg/L. The flow may be turbulent (e.g., may have a Reynolds number higher than 2300, such as in a range of from 3500 to 100,000). The flow may be obtained from an output of an atomization chamber. A gas flow rate of the flow may be in the range of from ten to one hundred liters per minute. A concentration of the liquid droplets in the flow may vary over time (e.g., at a frequency in the range of from three to three hundred cycles per minute). Such variation may for example be produced by providing the liquid to the atomization chamber as pulsed discharges while providing the gas to the atomization chamber as a continuous flow. The injecting may be performed continuously over a duration in the range of, for example, from sixty to six hundred seconds.

After the endoscope has been cleaned, it may undergo a high-level disinfection (HLD) routine as well. The HLD routine may include soaking the endoscope in a disinfecting solution that contains at least one high-level disinfectant. The high-level disinfectant may for example be configured to eliminate microorganisms (e.g. bacteria, viruses, mycobacteria, fungi, bacterial endospores, etc.) in or on the endoscope or a part thereof. Examples of high-level disinfectants that may be contained in the disinfecting solution include glutaraldehyde (e.g., at a concentration of 2% or more, 2.4% or more, 3% or more), ortho-phthalaldehyde (OPA; e.g., at a concentration of 0.5% or higher, 0.55% or higher, 0.6% or higher), and peracetic acid (e.g., at a concentration of between 0.1% and 0.3%, e.g. about 0.2%; alternatively, a concentration of at least 1820 mg/L).

After cleaning and/or after HLD, one or more channels of the endoscope (e.g., any one or more of the endoscope channels described herein) may be dried. Such drying may be gravity-based and may be performed by hanging the endoscope in a drying cabinet (and possibly circulating, within the cabinet and possibly at a positive pressure, air that is heated, dried, filtered, and/or sterilized). In another example, the one or more channels may be dried by injecting a gas at a low flow rate (e.g., in a range of from one to twenty liters per minute) at a low to moderate temperature (e.g., in a range of from ten to thirty degrees Celsius) to remove residual water (e.g., for a duration of from ten to sixty seconds), and then at a high flow rate (e.g., in a range of from twenty to one hundred liters per minute) at a moderate to high temperature (e.g., in a range of from thirty to sixty degrees Celsius) (e.g., for a duration of from thirty to 150 seconds). The gas may comprise or consist essentially of, for example, at least one of dinitrogen or air. During the high-flow-rate period, the gas may be a plasma (e.g., generated by an electrical discharge in a flow of dinitrogen or air), which may disinfect the channel. In such case, the temperature of the plasma may be in a range of from twenty to eighty degrees Celsius (e.g., in a range of from thirty to fifty degrees Celsius), and a duration of the plasma-injecting period may be in a range of from five to sixty seconds.

Figure 5A:
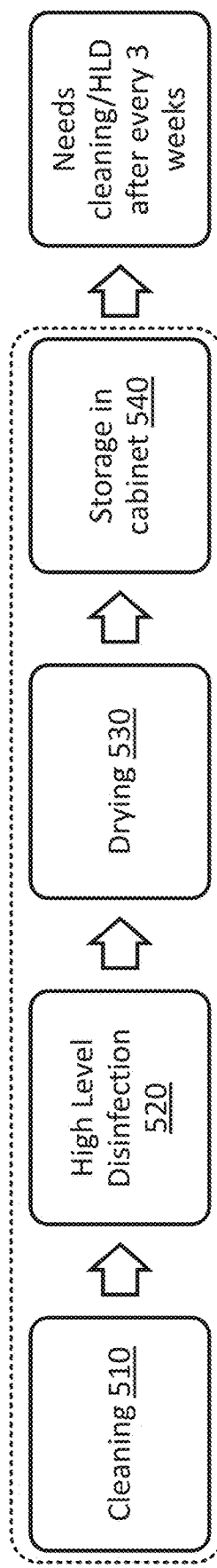
FIG. 5A shows a flowchart of a process 500 of reprocessing an endoscope in accordance with some embodiments.

FIG. 5A shows a flowchart of a process 500 of reprocessing an endoscope (e.g., endoscope 100) that includes cleaning the endoscope (e.g., according to any of the examples described above) (block 510), performing an HLD routine on the endoscope (e.g., according to any of the examples described above) (block 520); drying the endoscope (e.g., according to any of the examples described above) (block 530); and storing the endoscope in a cabinet (e.g., according to any of the examples described above) (block 540). If such a process is performed using a liquid chemical sterilant (LCS) (e.g., peracetic acid), a six-log or greater reduction in the number of bacterial endospores may be achieved, and the process may be called "just-in-time" (JIT) sterilization. One example of an LCS system that may be used for JIT sterilization is the Steris System 1E (Steris, Mentor, OH). Health and safety regulations may require endoscopes that are reprocessed using JIT sterilization to be reprocessed again before use if more than three weeks has passed since the HLD routine 520 was performed.

Methods for sterilization of medical devices include autoclaving (e.g., sterilization using steam under pressure). Flexible endoscopes are heat-labile devices, however, which may become irreversibly damaged if temperature limits are exceeded. A colonoscope, gastroscope, or duodenoscope may be damaged, for example, if reprocessed at a temperature that exceeds 75 or even sixty degrees Celsius.

Figure 5B:
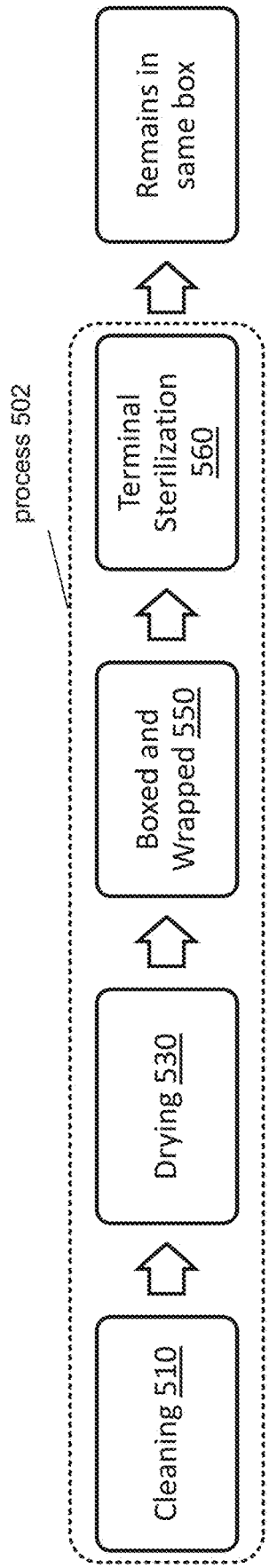
FIG. 5B shows a flowchart of a process 502 of reprocessing an endoscope in accordance with some embodiments.

Additionally or alternatively to HLD, it may be desired to sterilize the endoscope (e.g., endoscope 100) using a low-temperature sterilization process. FIG. 5B shows a flowchart of a process 502 of reprocessing an endoscope (e.g., endoscope 100) that includes cleaning the endoscope (e.g., according to any of the examples described above) (block 510), drying the endoscope (e.g., according to any of the examples described above) (block 530); boxing and wrapping the endoscope (block 550); and subjecting the endoscope to a low-temperature terminal sterilization process (block 560). The term "terminal sterilization" indicates a process that has been demonstrated to achieve at least a twelve-log reduction of bacterial endospores (e.g., has been validated with a sterilization assurance level (SAL) of not more than $10^{-6}$). As used herein, the term "terminally sterilized endoscope" indicates an endoscope that has been sterilized using a process has been validated with a sterilization assurance level (SAL) of not more than $10^{-6}$.

Boxing and wrapping of the endoscope (block 550) may include packaging the endoscope in a sterilization wrap before subjecting the endoscope to the low-temperature terminal sterilization process of block 560. If the endoscope remains wrapped after the sterilization process of block 560 is completed, the sterile life of the endoscope may be as long as three to six months. The sterilization wrap may be made of (e.g., comprises or consists of) one or more nonwoven materials, such as multiple layers of extruded fibers (e.g., extruded polyolefin fibers). In some examples, the sterilization wrap comprises one or more meltblown interior layers of extruded polyolefin fibers enclosed between two spun-bonded exterior layers of extruded polyolefin fibers. One example of such a product is the Halyard SMART-FOLD* Sterilization Wrap (Owens & Minor, Richmond, VA).

One example of the low-temperature terminal sterilization process of block 560 includes confining the endoscope within a humid sterilizing atmosphere of ethylene oxide (EtO), typically at a temperature between 37 and 63 degrees Celsius, for a specified period (e.g., one to six hours). Due to the high toxicity of EtO, however, such a process also requires a subsequent degassing period of up to 48 hours before the endoscope may be used.

Another example of the low-temperature sterilization process of block 560 includes confining the endoscope within a sterilizing atmosphere of vaporized hydrogen peroxide (VHP) for a specified period (e.g., sixty to seventy minutes). Such a process may use a high concentration (for example between 50% and 70%, e.g., 59%) of hydrogen peroxide and/or may be performed in a vacuum (e.g., at a pressure of 14 Torr or less). The temperature at which such a process is performed may be below about 70 degrees Celsius (e.g., below about 65, 60, or 55 degrees Celsius). One example of a VHP system that may be used for terminal sterilization is the Steris VPro Max (Steris, Mentor, OH). Such a process may include applying an electrical field to the sterilization chamber to generate a plasma, and in such case the duration of exposure of the endoscope to the plasma may be in the range of from five to thirty minutes. One example of a VHP system that includes such plasma generation and may be used for terminal sterilization is the Sterrad 100NX (Advanced Sterilization Products, Irvine, CA).

As mentioned above, lubrication of the LCB and/or of the angulation wire(s) of an endoscope is important for avoiding damage to the endoscope and for achieving a desired articulation performance. Molybdenum disulfide is a solid lubricant that is commonly used for both purposes. Unfortunately, molybdenum disulfide is incompatible with the use of vaporized hydrogen peroxide for endoscope sterilization, as molybdenum disulfide may react with vaporized hydrogen peroxide to form sulphuric acid and sulphurous acid. These acids may attack elastomeric and other components of the endoscope and may cause the elastomers to become brittle, to become degraded, and/or to develop cracks after as few as eight or twelve sterilization cycles.

It may be desired to lubricate the LCB and/or angulation wire(s) of an endoscope without using any molybdenum disulfide. For this, the endoscope may comprise a first lubricant that lubricates the LCB. The first lubricant may comprise at least one solid lubricant and may be free of (e.g., not contain any) molybdenum disulfide. In one example, a mixture (e.g., a suspension or dispersion) of carbon fluoride (graphite fluoride) in silicone oil is used as the first lubricant to lubricate the LCB of a peroxide-resistant endoscope (e.g., endoscope 100). Such a mixture may be used, for example, in place of a lubricant that contains molybdenum disulfide. Such a mixture may be used to coat the fibers of the LCB and/or to coat the inner surface of the casing of the LCB. Alternatively or additionally, such a mixture may also be used to coat the outer surface of the casing of the LCB. One example of a carbon fluoride that may be suitably used in such a mixture has the trade name CEFBON CMC (Central Glass Co., Ltd., Tokyo, JP) and is characterized by a fluorine content of 62 to 64 percent by weight and an average particle diameter of 5 microns. In other examples, a carbon fluoride with a different fluorine content and/or a different average particle diameter may be used. The fluorine content may for example be no less than 40 percent by weight, in some examples no less than 50 percent by weight, in one example no less than 60 percent by weight and/or may be no more than 80 percent by weight, in some examples no more than 70 percent by weight, in one example no more than 65 percent by weight. The average particle diameter may for example be no less than 2 microns, in some examples no less than 4 microns and/or may be no more than 10 microns, in some examples no more than 6 microns.

Alternatively, the first lubricant may comprise at least one solid lubricant (e.g., according to any of the examples described in the previous paragraph) and may also contain a small amount (e.g., not more than fifteen or twenty percent by weight) of molybdenum disulfide. In one example, the amount of molybdenum disulfide in the first lubricant does not exceed ten percent by weight, as an endoscope 100 has described herein has been shown to be peroxide-resistant for up to 125 reprocessing cycles even with such an amount of molybdenum disulfide in the first lubricant. In another example, the amount of molybdenum disulfide in the first lubricant does not exceed five percent by weight, and in a further example, the amount of molybdenum disulfide in the first lubricant does not exceed two percent by weight.

Additionally or alternatively, the endoscope may comprise a second lubricant that lubricates the angulation wire(s). The second lubricant may comprise at least one solid lubricant and may be free of (e.g., not contain any) molybdenum disulfide. In some examples, the second lubricant may be different from the first lubricant. In one example, nanographite is used as the second lubricant to lubricate one or more (possibly all) of the angulation wire(s) of a peroxide-resistant endoscope (e.g., endoscope 100). Such a lubricant may be used, for example, in place of a lubricant that contains molybdenum disulfide. The nanographite may have an average particle size in the range of from 0.2 to 50 microns, in some examples in the range of from 1 micron to 30 microns, in one example in the range of from 5 microns to 20 microns.

In another example, a mixture of nanographite and powdered PTFE is used as the second lubricant to lubricate one or more (possibly all) of the angulation wire(s) of a peroxide-resistant endoscope (e.g., endoscope 100). Such a mixture may be used, for example, in place of a lubricant that contains molybdenum disulfide. The nanographite in the mixture may have an average particle size in the range of from 0.2 to 50 microns, in some examples in the range of from 1 micron to 30 microns, in one example in the range of from 5 microns to 20 microns. The powdered PTFE in the mixture may have an average particle size in the range of from 0.1 to 50 microns, in some examples in the range of from 1 micron to 30 microns, in one example in the range of from 5 microns to 20 microns.

Alternatively, the second lubricant may comprise at least one solid lubricant (e.g., according to any of the examples described in the previous two paragraphs) and may also contain a small amount (e.g., not more than fifteen or twenty percent by weight) of molybdenum disulfide. In one example, the amount of molybdenum disulfide in the second lubricant does not exceed ten percent by weight; in another example, the amount of molybdenum disulfide in the second lubricant does not exceed five percent by weight; and in a further example, the amount of molybdenum disulfide in the second lubricant does not exceed two percent by weight.

Even in the absence of molybdenum disulfide, the strongly oxidizing effect of an atmosphere of vaporized hydrogen peroxide may degrade components of an endoscope (e.g., elastomers, adhesives), and it is also possible that free radicals generated by the use of a plasma may degrade components that would otherwise be resistant to oxidation by the vaporized hydrogen peroxide. Accordingly, it may be desired to implement the elastomeric (e.g., rubber) components of endoscope 100 using peroxide-resistant materials.

In the endoscope 100, the outer casings of the insertion tube 112 and/or the umbilical cord 190 may be made of (e.g. comprise or consist of) polyurethane, which is resistant to degradation by repeated exposure to an atmosphere of vaporized hydrogen peroxide. Although polyurethane is inexpensive and nonreactive, it may be insufficiently flexible to be used for other parts of a peroxide-resistant endoscope, such as the outer casing of the bending portion and the strain relief boots. It may be desired to use a peroxide-resistant material that is more flexible than polyurethane for such parts of the endoscope, such as fluorocarbon rubber or silicone rubber.

In one example, the outer casing of the bending portion 118 of the endoscope 100 is made of (e.g. comprises or consists of) fluorocarbon rubber. In some examples, the outer casing of the bending portion 118 may consist essentially of fluorocarbon rubber, which means that the outer casing may also contain additives other than fluorocarbon rubber that do not materially affect its resistance to VHP or to products of a reaction of molybdenum disulfide with VHP. For example, a fluorocarbon rubber content of the outer casing of the bending portion 118 may be at least 80 percent by weight, in some examples at least 90 percent by weight, in one example at least 95 percent by weight and in one example at least 98 percent by weight. The fluorocarbon rubber may be cross-linked in three dimensions.

Alternatively or additionally, one or more of the strain relief boots of a peroxide-resistant endoscope may be made of (e.g. comprise or consist of) silicone rubber. For example, one or more of the strain relief boots 132, 134, and 172 of the endoscope 100 may be made of silicone rubber. In some examples, one or more of the strain relief boots may consist essentially of silicone rubber, which means that the strain relief boot(s) may also contain additives other than silicone rubber that do not materially affect its resistance to VHP or to products of a reaction of molybdenum disulfide with VHP. For example, a silicone rubber content of the respective strain relief boot(s) may be at least 80 percent by weight, in some examples at least 90 percent by weight, in one example at least 95 percent by weight and in one example at least 98 percent by weight. Other flexible components of the endoscope 100 that may be made of silicone rubber may include the covers of each of one or more control buttons of the control portion 130 and/or one or more port covers.

Other components of an endoscope that may degrade (e.g., peel, crack, deform or discolor) upon repeated exposure to vaporized hydrogen peroxide may include adhesives and coatings. It may be desired to implement one or more adhesives or coatings of the endoscope 100 using epoxy compounds. In one example, the adhesive 218 that secures the illumination window 217 to the body 215 of the distal tip 214 is an epoxy adhesive. The epoxy adhesive may be a two-component adhesive comprising a base resin and a curing agent (e.g., a hardener) and may also comprise other components (e.g., one or more fillers (e.g., silica) or colorants (e.g., carbon black)). The base resin may comprise, for example, a bisphenol A epoxy resin (e.g., bisphenol A, epichlorohydrin polymer; also called bisphenol type A liquid epoxy resin, CAS no. 25068-38-6, or Japan ENCS no. 7-1283). The curing agent may comprise, for example, polyamide amine. The ratio of base resin to curing agent (by weight) in the epoxy adhesive may be more than two to one, in some examples may be at least 2.5 to one, and in some examples may be at least 2.8 or 2.9 to one. In these or other examples, the ratio of base resin to curing agent (by weight) in the epoxy adhesive may be not more than four to one, in some such examples may be not more than 3.5 to one, and in some such examples may be not more than 3.2 or 3.1 to one. The bending portion 118 may be secured to the insertion tube 112 at least in part by an epoxy adhesive (e.g., an epoxy adhesive according to any of the examples described above). The distal tip 114 (e.g., distal tip 214) may be secured to the bending portion 118 at least in part by an epoxy adhesive (e.g., an epoxy adhesive according to any of the examples described above).

In any of these cases, curing of the adhesive bond may comprise maintaining a temperature of the joint to which the epoxy adhesive has been applied within a cure temperature range for a cure period. The cure temperature range may be, for example, within one, two, five, or ten percent of a cure point temperature. In some examples, the cure point temperature may be 75 degrees Celsius; in other examples, the cure point temperature may be 80 degrees Celsius; in other examples, the cure point temperature may be 85 degrees Celsius; in other examples, the cure point temperature may be 90 degrees Celsius. The cure period may be at least ninety minutes, in some examples at least 115 minutes, in some examples at least 120 minutes, in some examples at least 115 minutes and not more than 135 minutes.

Additionally or alternatively, the adhesive that secures the electrical contacts 176 to the housing 184 of the interface portion 170 may be an epoxy adhesive (e.g., an epoxy adhesive according to any of the examples described above). In some examples, an epoxy coating (e.g., a two-component epoxy adhesive in which the ratio of base resin to curing agent (by weight) may be more than two to one, in some examples may be at least 2.5 to one, and in some examples may be at least 2.8 or 2.9 to one, and which may be not more than four to one, in some such examples may be not more than 3.5 to one, and in some such examples may be not more than 3.2 or 3.1 to one) may be used to coat the outer surface of the casing of the insertion tube 112 and/or to coat a junction (e.g., a bond) between the casings of the insertion tube 112 and the bending portion 118.

Other components of an endoscope that may degrade (e.g., peel, crack, deform, or discolor) upon repeated exposure to vaporized hydrogen peroxide include metal components and plastic components. It may be desired to implement such components using peroxide-resistant materials such as, for example, stainless steel, polyphenylene oxide, polyolefin, or polyethylene terephthalate (PET). In one example, one or more ports and/or connectors of the interface portion 170, one or more ports of the control portion 130, and/or the body 215 of the distal tip 214 are made or formed of stainless steel. Additionally or alternatively, the housing 184 of the interface portion, the housing of the control portion 130, and/or one or more actuators (e.g., one or more control knobs and/or levers) of the control portion 130 may be made of (e.g. comprise or consist of) polyphenylene oxide. In some examples, one or more plastic labels on the interface portion 170 and/or on the control portion 130 (e.g., indicating model number, serial number, directions, warnings, etc.) may be made of (e.g. comprise or consist of) polyolefin and/or PET.

The principles described herein may be practiced as described to obtain implementations of endoscopes that provide advantages such as resistance to degradation (e.g., a lack of any of peeling, cracking, deformation, discoloring, or failure of watertightness) even after multiple cycles of exposure to an atmosphere of vaporized hydrogen peroxide.

Typically a process of sterilizing an endoscope by confining it within an atmosphere of vaporized hydrogen peroxide as described above requires the cleaned reusable medical device to be extremely dry, as residual fluid may interfere with the sterilization process. Accordingly, it may be desired to dry the endoscope after cleaning is completed and before sterilization using vaporized hydrogen peroxide is begun. Such drying may include gravity-based drying as described above (e.g., within a drying cabinet) and/or may include drying by injecting a gas into one or more (e.g., all of the) channels of the endoscope as also described above (e.g., at a low flow rate and a low to moderate temperature, and then at a high flow rate and a moderate to high temperature). After the drying is completed, the process of sterilizing the endoscope by confining it within an atmosphere of vaporized hydrogen peroxide may be performed. After the process of sterilizing is completed, no further drying is performed.

In some examples, a peroxide-resistant flexible endoscope according to any of the embodiments described herein (e.g., endoscope 100) is reprocessed by performing one or more cleaning processes (e.g., soaking, brushing, wiping, and/or injecting a flow of a dispersion as described herein, and/or one or more other cleaning processes) followed by one or more HLD processes (e.g., an HLD routine as described herein and/or one or more other HLD processes). In other examples, a peroxide-resistant flexible endoscope according to any of the embodiments described herein (e.g., endoscope 100) is reprocessed by performing one or more cleaning processes (e.g., soaking, brushing, wiping, and/or injecting a flow of a dispersion as described herein, and/or one or more other cleaning processes) followed by one or more sterilization processes (e.g., confining the endoscope within a sterilizing atmosphere of vaporized hydrogen peroxide, and/or one or more other sterilization processes).

Further exemplary embodiments are provided below:

Example 1 includes an endoscope comprising an interface portion; a control portion coupled to the interface portion; an insertion portion coupled to the control portion, the insertion portion comprising a bending portion, an insertion tube extending from a distal end of the control portion to a proximal end of the bending portion, and a distal tip at a distal end of the bending portion; and a light carrying bundle (LCB) that extends from the interface portion to the distal tip. In this Example, an outer casing of the bending portion consists essentially of fluorocarbon rubber, a first lubricant that lubricates the LCB comprises at least one solid lubricant and does not contain more than ten percent by weight of molybdenum disulfide, and an outer casing of the insertion tube is bonded to the outer casing of the bending portion by a first cured epoxy adhesive, and, immediately before curing of the first epoxy adhesive: the first epoxy adhesive comprises a first base resin component and a first curing agent, and a ratio of the first base resin component to the first curing agent in the first epoxy adhesive is at least 2.5 (two-and-one-half) to one by weight.

Example 2 includes the endoscope according to Example 1, wherein the outer casing of the insertion tube comprises polyurethane.

Example 3 includes the endoscope according to any of Examples 1 and 2, wherein the at least one solid lubricant of the first lubricant comprises a carbon fluoride.

Example 4 includes the endoscope according to any of Examples 1-3, wherein the first lubricant comprises a silicone oil.

Example 5 includes the endoscope according to any of Examples 1-4, wherein the outer casing of the bending portion is bonded to the distal tip by a second epoxy adhesive.

Example 6 includes the endoscope according to any of Examples 1-5, wherein the distal tip comprises a body and at least one piece of optical glass, and wherein the at least one piece of optical glass is bonded to the body by a third epoxy adhesive.

Example 7 includes the endoscope according to Example 6, wherein the body of the distal tip is formed of stainless steel.

Example 8 includes the endoscope according to any of Examples 6 and 7, wherein the at least one piece of optical glass is bonded to the LCB.

Example 9 includes the endoscope according to any of the preceding Examples, the endoscope further comprising at least one angulation wire that extends through the insertion portion and is configured to transfer a force to cause the distal tip to move relative to the insertion tube, wherein a second lubricant that lubricates the at least one angulation wire includes at least one solid lubricant and does not contain more than ten percent by weight of molybdenum disulfide.

Example 10 includes the endoscope according to Example 9, wherein the at least one solid lubricant of the second lubricant comprises nanographite.

Example 11 includes the endoscope according to any of Examples 9 and 10, wherein the at least one solid lubricant of the second lubricant comprises polytetrafluoroethylene (PTFE).

Example 12 includes the endoscope according to any of the preceding Examples, wherein the endoscope further comprises a coating film that covers an exterior surface of the outer casing of the insertion tube and comprises a flexible epoxy adhesive.

Example 13 includes the endoscope according to any of the preceding Examples, wherein the endoscope further comprises a strain relief boot that is bonded to the control portion and to the insertion portion and consists essentially of silicone rubber.

Example 14 includes the endoscope according to any of the preceding Examples, wherein the first lubricant does not contain more than two percent by weight of molybdenum disulfide.

Example 15 includes a method of reprocessing the endoscope according to any of Examples 1-14, the method comprising exposing the endoscope to an atmosphere containing vaporized hydrogen peroxide.

Example 16 includes the method of Example 15, the method further comprising exposing an interior lumen of at least one channel of the endoscope to at least one of: a disinfecting solution that contains at least one high-level disinfectant, or a cleaning solution that contains at least one detergent or enzymatic cleaning agent.

Example 17 includes the method of Example 16, the method further comprising, subsequent to the exposing the interior lumen of the at least one channel to at least one of a disinfecting solution and a cleaning solution, and prior to exposing the endoscope to the atmosphere containing vaporized hydrogen peroxide, drying the endoscope.

Example 18 includes the method of Example 15, the method further comprising, prior to exposing the endoscope to the atmosphere containing vaporized hydrogen peroxide, drying the endoscope.

Example 19 includes the method of any of Examples 17 and 18, wherein the drying the endoscope comprises hanging the endoscope in a drying cabinet.

Example 20 includes the method of any of Examples 17 and 18, wherein the drying the endoscope comprises injecting a gas into one or more channels of the endoscope.

Example 21 includes the method of Example 20, wherein the drying the endoscope comprises injecting the gas into the one or more channels at a flow rate in a range of from one to twenty liters per minute and a temperature in a range of from ten to thirty degrees Celsius, followed by injecting the gas into the one or more channels at a flow rate in a range of from twenty to one hundred liters per minute and a temperature in a range of from thirty to sixty degrees Celsius.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. For the purposes of the present document, the phrase "A is based on B" means "A is based on at least B." As used herein, the term "substantially," "approximately," or "about" may be substituted with "within [a percentage] of" what is specified, where the percentage includes 0.1, 1, 5, and 10 percent. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

The invention claimed is:

1. An endoscope comprising:
   an interface portion;
   a control portion coupled to the interface portion;
   an insertion portion coupled to the control portion, the insertion portion comprising:
   a bending portion,
   an insertion tube extending from a distal end of the control portion to a proximal end of the bending portion, and
   a distal tip at a distal end of the bending portion; and
   a light carrying bundle (LCB) that extends from the interface portion to the distal tip, wherein:
an outer casing of the bending portion consists essentially of fluorocarbon rubber,
a first lubricant that lubricates the LCB comprises at least one solid lubricant and does not contain more than ten percent by weight of molybdenum disulfide, and
an outer casing of the insertion tube is bonded to the outer casing of the bending portion by a first cured epoxy adhesive, and
wherein, immediately before curing of the first epoxy adhesive:
the first epoxy adhesive comprises a first base resin component and a first curing agent, and
a ratio of the first base resin component to the first curing agent in the first epoxy adhesive is at least 2.5 (two-and-one-half) to one by weight;
wherein the outer casing of the bending portion is bonded to the distal tip by a second epoxy adhesive.

2. The endoscope according to claim 1, wherein the outer casing of the insertion tube comprises polyurethane.

3. The endoscope according to claim 1, wherein the at least one solid lubricant of the first lubricant comprises a carbon fluoride.

4. The endoscope according to claim 1, wherein the first lubricant comprises a silicone oil.

5. The endoscope according to claim 1, wherein the distal tip comprises a body and at least one piece of optical glass, and
wherein the at least one piece of optical glass is bonded to the body by a third epoxy adhesive.

6. The endoscope according to claim 5, wherein the body of the distal tip is formed of stainless steel.

7. The endoscope according to claim 5, wherein the at least one piece of optical glass is bonded to the LCB.

8. The endoscope according to claim 1, the endoscope further comprising at least one angulation wire that extends through the insertion portion and is configured to transfer a force to cause the distal tip to move relative to the insertion tube,
wherein a second lubricant that lubricates the at least one angulation wire includes at least one solid lubricant and does not contain more than ten percent by weight of molybdenum disulfide.

9. The endoscope according to claim 8, wherein the at least one solid lubricant of the second lubricant comprises nanographite.

10. The endoscope according to claim 8, wherein the at least one solid lubricant of the second lubricant comprises polytetrafluoroethylene (PTFE).

11. The endoscope according to claim 1, wherein the endoscope further comprises a coating film that covers an exterior surface of the outer casing of the insertion tube and comprises a flexible epoxy adhesive.

12. The endoscope according to claim 1, wherein the endoscope further comprises a strain relief boot that is bonded to the control portion and to the insertion portion and consists essentially of silicone rubber.

13. The endoscope according to claim 1, wherein the first lubricant does not contain more than two percent by weight of molybdenum disulfide.

14. A method of reprocessing the endoscope according to claim 1, the method comprising exposing the endoscope to an atmosphere containing vaporized hydrogen peroxide.

15. The method of claim 14, the method further comprising exposing an interior lumen of at least one channel of the endoscope to at least one of:
a disinfecting solution that contains at least one high-level disinfectant, or
a cleaning solution that contains at least one detergent or enzymatic cleaning agent.

16. The method of claim 15, the method further comprising, subsequent to the exposing the interior lumen of the at least one channel to at least one of a disinfecting solution and a cleaning solution, and prior to exposing the endoscope to the atmosphere containing vaporized hydrogen peroxide, drying the endoscope.

17. The method of claim 16, wherein the drying the endoscope comprises hanging the endoscope in a drying cabinet.

18. The method of claim 16, wherein the drying the endoscope comprises injecting a gas into one or more channels of the endoscope.

19. The method of claim 18, wherein the drying the endoscope comprises injecting the gas into the one or more channels at a flow rate in a range of from one to twenty liters per minute and a temperature in a range of from ten to thirty degrees Celsius, followed by injecting the gas into the one or more channels at a flow rate in a range of from twenty to one hundred liters per minute and a temperature in a range of from thirty to sixty degrees Celsius.

20. The method of claim 14, the method further comprising, prior to exposing the endoscope to the atmosphere containing vaporized hydrogen peroxide, drying the endoscope.

\* \* \* \* \*